(12) United States Patent
Ouchi

(10) Patent No.: US 6,656,132 B1
(45) Date of Patent: Dec. 2, 2003

(54) ENDOSCOPIC TISSUE COLLECTING INSTRUMENT

(75) Inventor: Teruo Ouchi, Saitama (JP)

(73) Assignee: Pentex Corporation, Tokyo (JP)

( * ) Notice: Subject to any disclaimer, the term of this patent is extended or adjusted under 35 U.S.C. 154(b) by 0 days.

(21) Appl. No.: 09/722,730

(22) Filed: Nov. 28, 2000

(30) Foreign Application Priority Data

Nov. 29, 1999 (JP) .......................................... P.11-336915

(51) Int. Cl.<sup>7</sup> ............................................... A61B 10/00
(52) U.S. Cl. ........................ 600/564; 600/566; 600/567; 606/170
(58) Field of Search ................. 600/562, 564–567, 600/104; 606/167, 170; 604/19, 22, 164.01, 164.11

(56) References Cited

U.S. PATENT DOCUMENTS

| | | | | |
|---|---|---|---|---|
| 3,606,878 A | * | 9/1971 | Kellogg, Jr. ................. | 600/566 |
| 4,530,356 A | * | 7/1985 | Helfgott et al. ............. | 606/171 |
| 4,660,267 A | * | 4/1987 | Wheeler ....................... | 29/437 |
| 4,702,260 A | * | 10/1987 | Wang .......................... | 600/566 |
| 4,790,329 A | * | 12/1988 | Simon ......................... | 600/562 |
| 4,799,494 A | * | 1/1989 | Wang .......................... | 600/566 |
| 4,961,430 A | * | 10/1990 | Sheahon ....................... | 600/567 |
| 5,320,110 A | * | 6/1994 | Wang .......................... | 600/566 |
| 5,339,828 A | * | 8/1994 | Keating et al. ............... | 600/572 |
| 5,458,112 A | * | 10/1995 | Weaver ........................ | 600/566 |
| 5,487,392 A | | 1/1996 | Haaga .......................... | 600/566 |
| 5,505,210 A | * | 4/1996 | Clement ....................... | 600/566 |
| 5,718,237 A | | 2/1998 | Haaga .......................... | 600/564 |
| 5,775,333 A | * | 7/1998 | Burbank et al. .............. | 600/567 |
| 6,419,641 B1 | * | 7/2002 | Mark et al. .................. | 600/564 |

FOREIGN PATENT DOCUMENTS

| | | |
|---|---|---|
| JP | 2994062 | 10/1992 |
| JP | 9-500565 | 1/1997 |
| JP | 10216134 | 8/1998 |

* cited by examiner

*Primary Examiner*—Charles A. Marmor, II
(74) *Attorney, Agent, or Firm*—Greenblum & Bernstein, P.L.C.

(57) ABSTRACT

An endoscopic tissue collecting instrument includes an outer sheath that has an annular blade portion formed on the outer periphery of its distal end and which has a tissue retaining recess formed in the lateral side of an area close to the blade portion, and an inner needle that is fitted into the outer sheath to be capable of moving back and forth along the longitudinal axis and which has formed at the distal end a cutting blade for cutting off the tissue entering the tissue retaining recess and a needle tip pointed forward. The inner needle can be manipulated by the operator to move back and forth between two positions, one being where its distal end is drawn into the outer sheath such that it does not close the tissue retaining recess and the other being where it protrudes from the distal end of the outer sheath.

11 Claims, 9 Drawing Sheets

ENDOSCOPIC TISSUE COLLECTING INSTRUMENT

BACKGROUND OF THE INVENTION

The present invention relates to an endoscopic tissue collecting instrument suitable for use typically in a biopsy of the pancreas and the liver by being inserted into and removed from a treatment instrument insertion channel in an endoscope.

Figure 10:
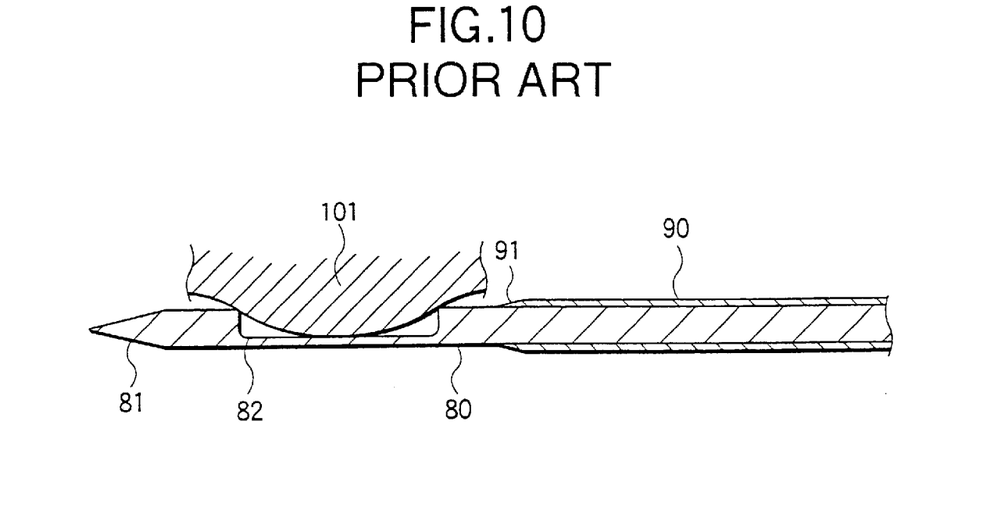
FIG. 10 is a longitudinal section showing the distal end portion of a conventional endoscopic tissue collecting instrument in a use mode.

FIG. 10 shows the distal end portion of a Menghini needle used as an endoscopic tissue collecting instrument. It comprises a rod-shaped needle shaft 80 having a pointed end 81 and a tissue retaining recess 82 formed in the lateral side of an area close to the needle end 81 and into which an excised tissue specimen 101 is retained.

A cannula or outer sheath 90 is fitted over the needle shaft 80 to be capable of moving back and forth along the longitudinal axis and it has an annular blade 91 formed on the inner circumference of the distal end for cutting off the tissue retained in the recess 82.

Before passage into the treatment instrument insertion channel of an endoscope, the endoscopic tissue collecting instrument is passed through a guide tube (not shown) typically made of a tetrafluoroethylene resin to prevent the needle tip 81 from damaging the insertion channel.

A problem with the above-described endoscopic tissue collecting instrument is that the depth of the tissue retaining recess 82 is inevitably much smaller than the diameter of the outer sheath 90, often causing a failure to collect an adequate amount of the tissue specimen.

SUMMARY OF THE INVENTION

An object, therefore, of the present invention is to provide an endoscopic tissue collecting instrument with which an adequate amount of the tissue specimen can be easily collected without increasing the diameter of the outer sheath.

According to the present invention, the tissue accommodated in the outer sheath via a tissue retaining recess formed in its lateral side can be used as a specimen for biopsy. The collected tissue specimen has the largest size that can be expected from the given diameter of the outer sheath. Hence, an adequate amount of the tissue specimen can be easily collected without increasing the diameter of the outer sheath.

In addition, since an inner needle is simply slid within the outer sheath to cut off the tissue specimen, sliding resistance is small, and the cutting operation can be done efficiently. An endoscopic tissue collecting instrument of a preferred embodiment includes:

an outer sheath including:
  an annular blade portion formed on an outer periphery of a distal end of the outer sheath to be directed forward; and
  a tissue retaining recess formed in a lateral side of an area close to the blade portion; and
  an inner needle that is fitted into the outer sheath to be capable of moving back and forth along a longitudinal axis, the inner needle including:
    a cutting blade, formed at a distal end of the inner needle, for cutting off a tissue entering the tissue retaining recess; and
    a needle tip formed at the distal end of the inner needle, and pointed forward, wherein:
    the inner needle can be manipulated from an operator side to move back and forth between two positions, one being where the distal end of the inner needle is drawn into the outer sheath such that it does not close the tissue retaining recess and the other being where it protrudes from the distal end of the outer sheath.

The distal end of the inner needle may be in the form of a tube, and the cutting blade may be formed on an inner periphery of the tube. The endoscopic tissue collecting instrument may further include an aspiration channel that communicates with the tissue retaining recess at a distal end thereof and which extends to a basal end of the outer sheath. In this case, the aspiration channel may be formed in the inner needle, and a connection socket for establishing connection to an aspirating device may be provided at a basal end of the inner needle.

The tissue retaining recess may be a cutout formed in the lateral side of said outer sheath. The endoscopic tissue collecting instrument may further include a guide tube through which the outer sheath is passed to be capable of moving back and forth along the longitudinal axis. The needle tip of the inner needle may also serve as the cutting blade.

The present disclosure relates to the subject matter contained in Japanese patent application No. Hei. 11-336915 (filed on Nov. 29, 2000), which is expressly incorporated herein by reference in its entirety.

DESCRIPTION OF THE PREFERRED EMBODIMENT

Several embodiments of the present invention are described below with reference to accompanying drawings.

Figure 1:
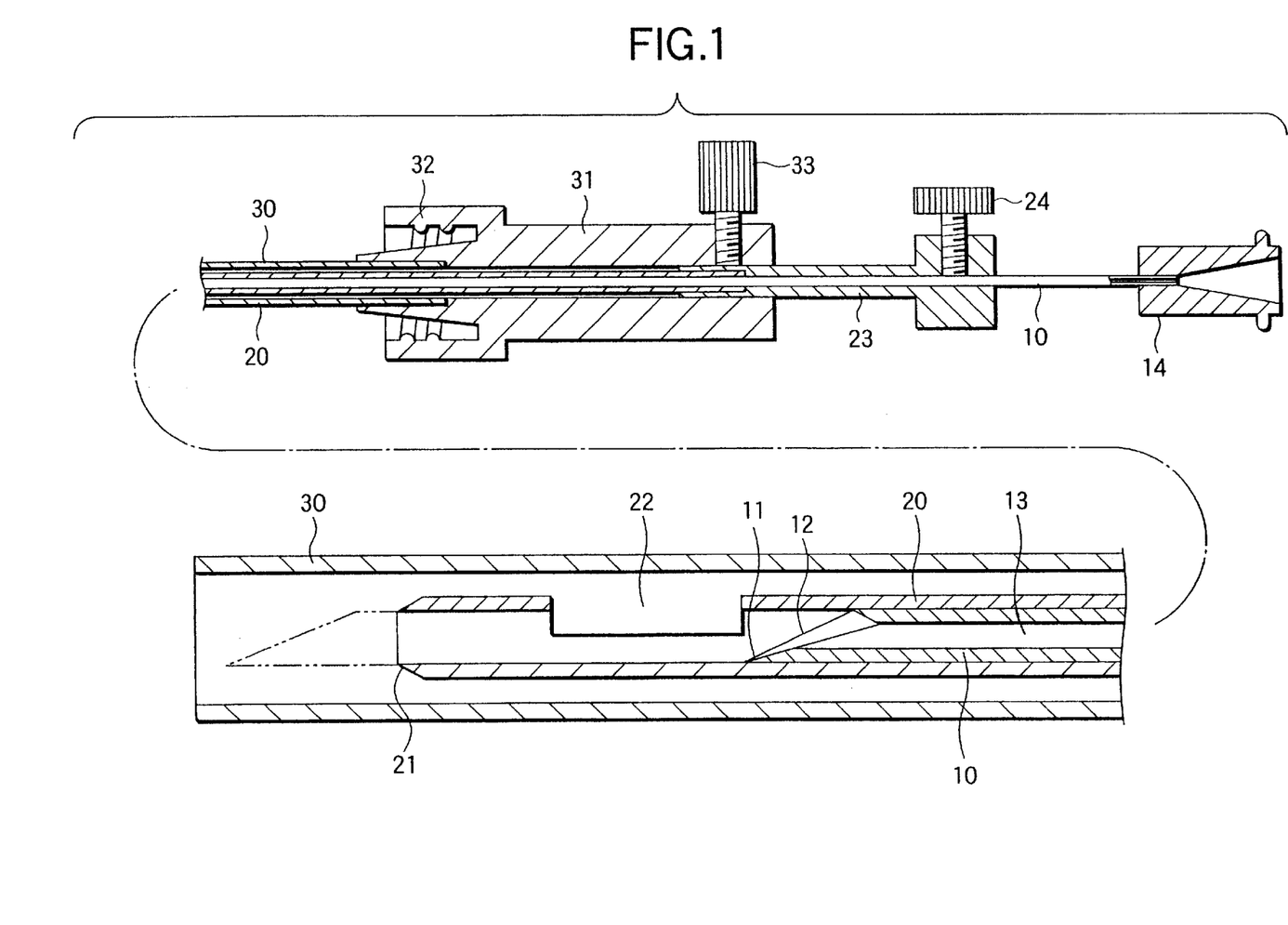
FIG. 1 is a longitudinal section showing the general layout of an endoscopic tissue collecting instrument according to the first embodiment of the invention.

FIG. 1 shows the general layout of an endoscopic tissue collecting instrument according to a first embodiment of the invention. A cannula or outer sheath 20 is formed as a round pipe having a constant diameter throughout its length. The outer sheath 20 has an annular blade portion 21 formed on the outer periphery of its distal end and directed forwards.

A tissue retaining recess 22 for retaining a tissue specimen in its interior is formed in the lateral side of the outer sheath 20 in an area immediately behind the blade portion 21. The tissue retaining recess 22 is formed by making a cutout in the lateral side of the pipe-like outer sheath 20 to a depth almost equal to its radius.

Figure 2:
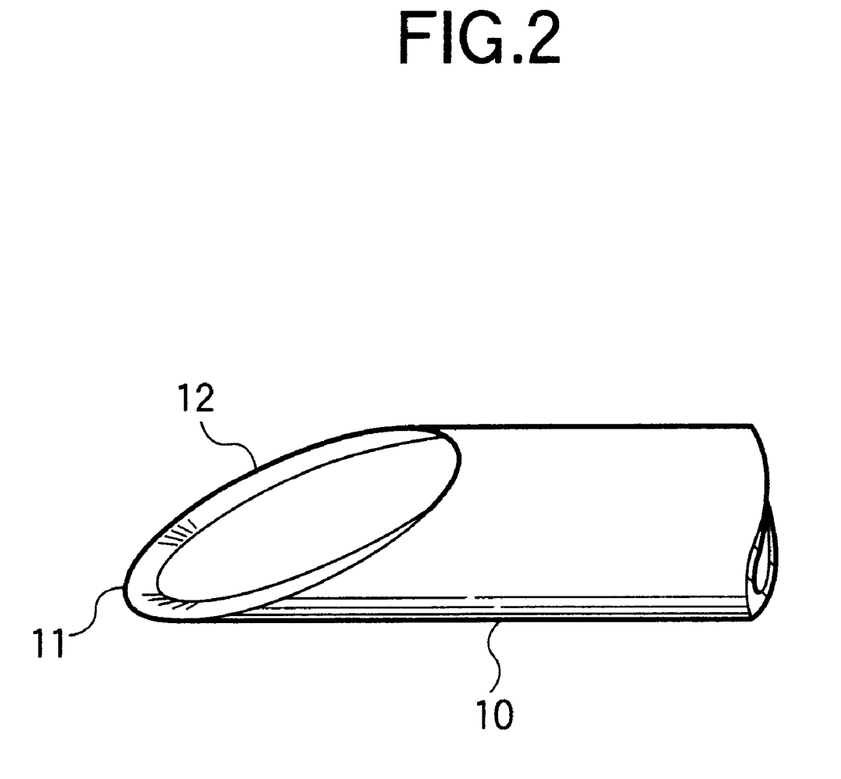
FIG. 2 is a perspective view showing the distal end portion of the inner needle according to the first embodiment of the invention.

A pipe-like inner needle 10 having a circular section is passed into the outer sheath 20 over the substantially entire length of the outer sheath 20 so that it is capable of moving back and forth along the longitudinal axis. As also shown in FIG. 2, the distal end portion of the inner needle 10 is skived (cut at an angle) as in the case of a syringe so that the projecting end provides a needle tip 11 that is pointed forward.

In order to cut off the tissue entering the tissue retaining recess 22, the distal end portion of the inner needle 10 is not simply skived but a sharp cutting blade 12 which is formed on the entire inner circumference. The needle tip 11 is continuous with the cutting blade 12.

The inner needle 10 can be manipulated by the operator to move back and forth between two positions, one being indicated by the solid line in FIG. 1 where its distal end is drawn into the outer sheath 20 such that it does not close the tissue retaining recess 22 and the other being indicated by the two-dotted chain line where it protrudes from the distal end of the outer sheath 20.

If the endoscopic tissue collecting instrument is to be used with a rigid endoscope, both the outer sheath 20 and the inner needle 10 are formed of a metal pipe; if it is to be used with a soft endoscope having a flexible part to be inserted into a body cavity, the two members may be formed of a flexible plastic material or a metal pipe (e.g. a stainless steel pipe) that is sufficiently thin-walled to have flexibility.

If a thin-walled stainless steel pipe is used, the outer sheath 20 may be sized to have an outside diameter of about 1.0 mm and an inside diameter of about 0.9 mm whereas the inner needle 10 may be sized to have an outside diameter of about 0.9 mm and an inside diameter of about 0.8 mm. With these dimensions, both members can be bent smoothly to permit use with a soft endoscope.

The inner needle 10 extends farther beyond the basal end of the outer sheath 20 toward the operator, and its basal end is fitted with a suction line socket 14 for establishing connection to an aspirating device such as a syringe. Thus, by applying suction to the socket 14, vacuum can be drawn from the tissue retaining recess 22 via an aspiration channel 13 defined by the bore of the inner needle 10.

A grip 23 attached to the basal end of the outer sheath 20 (the end which is closer to the operator) is made of a rigid material, and fitted with a first manual lock screw 24 for pressing and fixing the inner needle 10.

Because of this design, with the first lock screw 24 being tightened up, the outer sheath 20 and the inner needle 10 move back and forth as a unit. If the first lock screw 24 is loosened, the outer sheath 20 and the inner needle 10 can be moved back and forth independently of each other.

Indicated by 30 is a guide tube that protects the treatment instrument insertion channel of a soft endoscope from being damaged by the needle tip 11 while the endoscopic tissue collecting instrument is inserted into or removed from the insertion channel. The guide tube is typically made of a tetrafluoroethylene resin.

A support member 31 is securely coupled to the basal end of the guide tube 30 and it has a mount socket 32 with a female thread for establishing firm coupling to the treatment instrument insertion port of the endoscope. The support member 31 is also furnished with a second manual lock screw 33 that is capable of fixing the grip 23 in a desired position relative to the support member 31.

Figure 3:
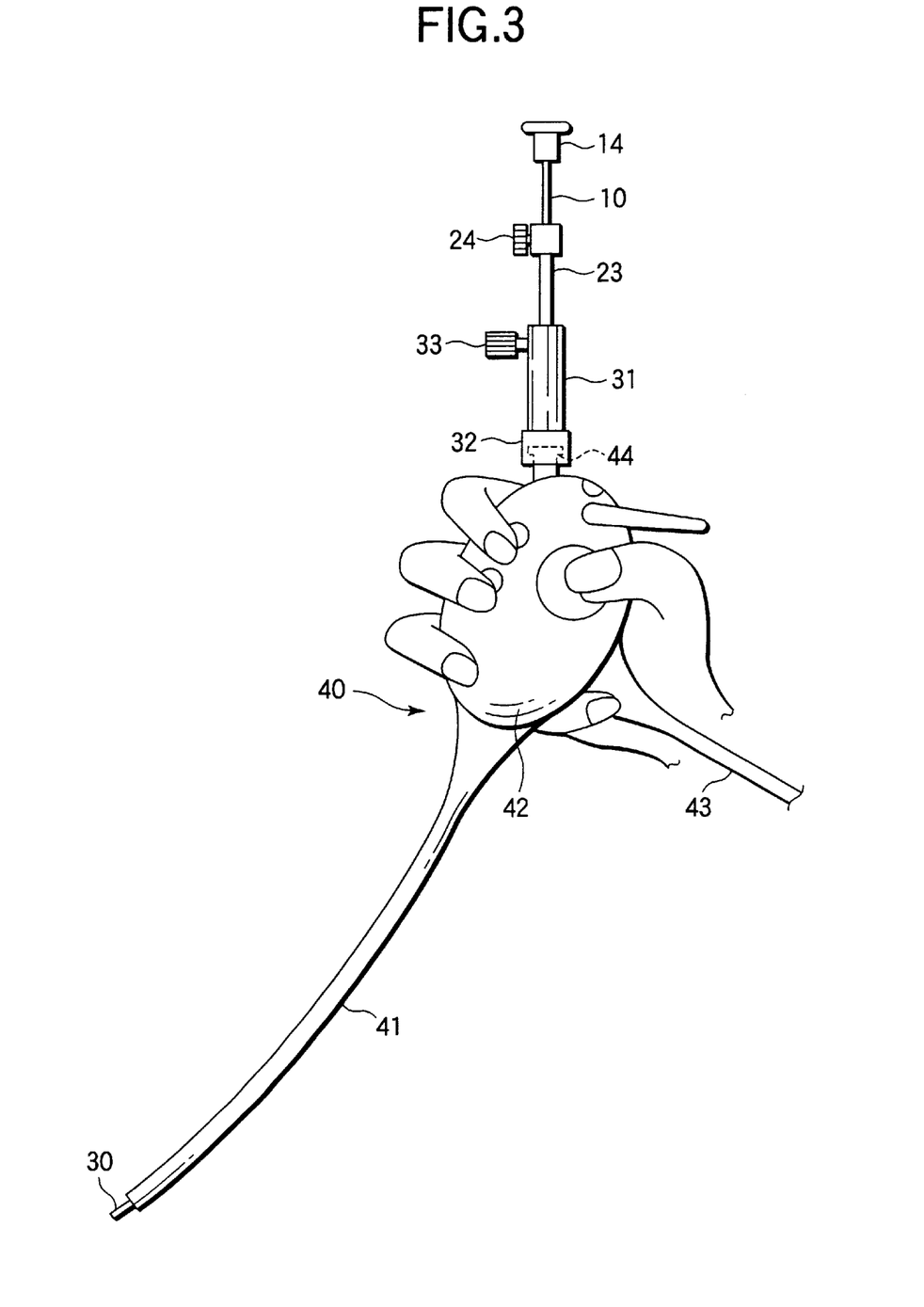
FIG. 3 is an exterior view showing how the endoscopic tissue collecting instrument according to the first embodiment of the invention is used as an attachment to a soft endoscope.

FIG. 3 shows the endoscopic tissue collecting instrument as it has been set on a soft endoscope 40. Reference numeral 41 designates the part which is encased in a flexible tube and which is to be inserted into a body cavity; 42 is the manipulating section; 43 is a connector to a video processor and light source unit; 44 is the treatment instrument insertion port.

With the second lock screw 33 held in a tightened position, the guide tube 30 is passed into the treatment instrument insertion channel of the endoscope and the mount socket 32 is held in engagement with the treatment instrument insertion port 44.

By loosening the first lock screw 24, the operator can manipulate the inner needle 10 to move back and forth without moving the outer sheath 20. If the second lock screw 33 is loosened and the operator manipulates the grip 23 to move it back and forth, the outer sheath 20 can accordingly be moved back and forth together with the inner needle 10.

Figure 4:
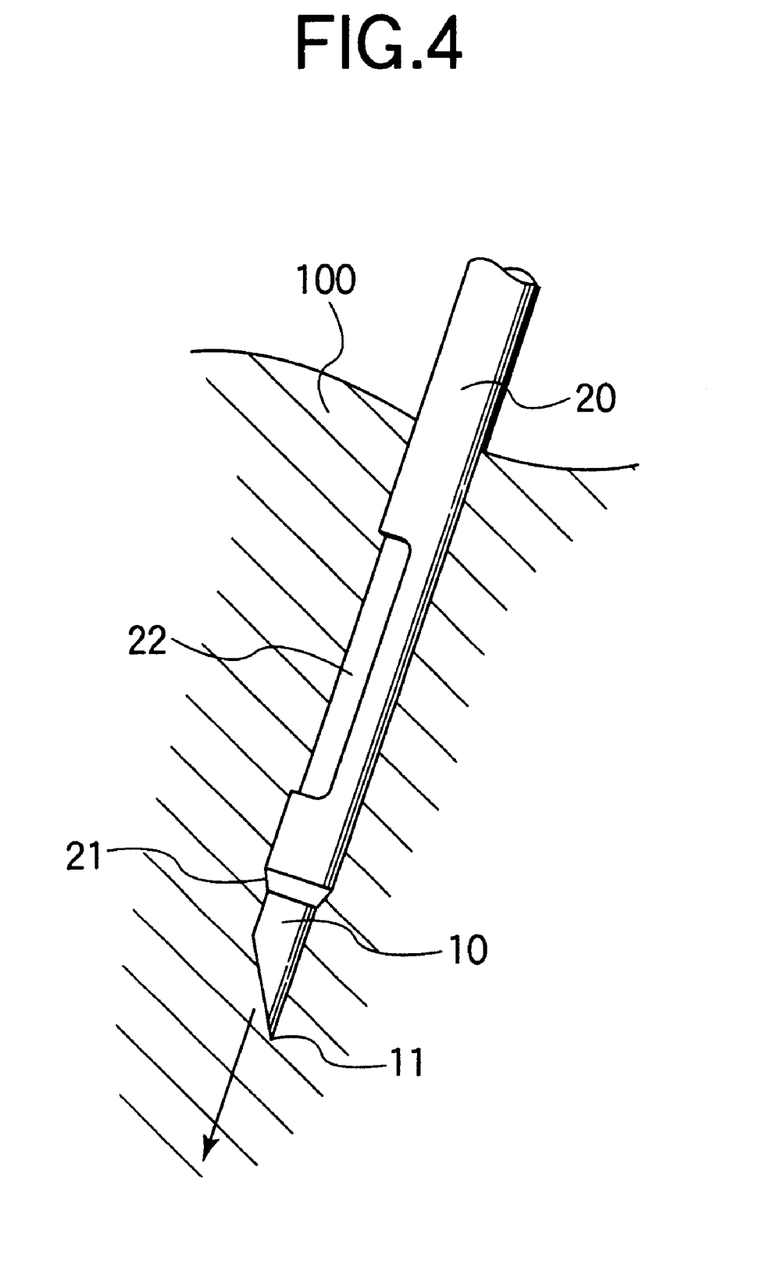
FIG. 4 is a longitudinal section showing the distal end portion of the endoscopic tissue collecting instrument as it is in the first phase of use.
Figure 5:
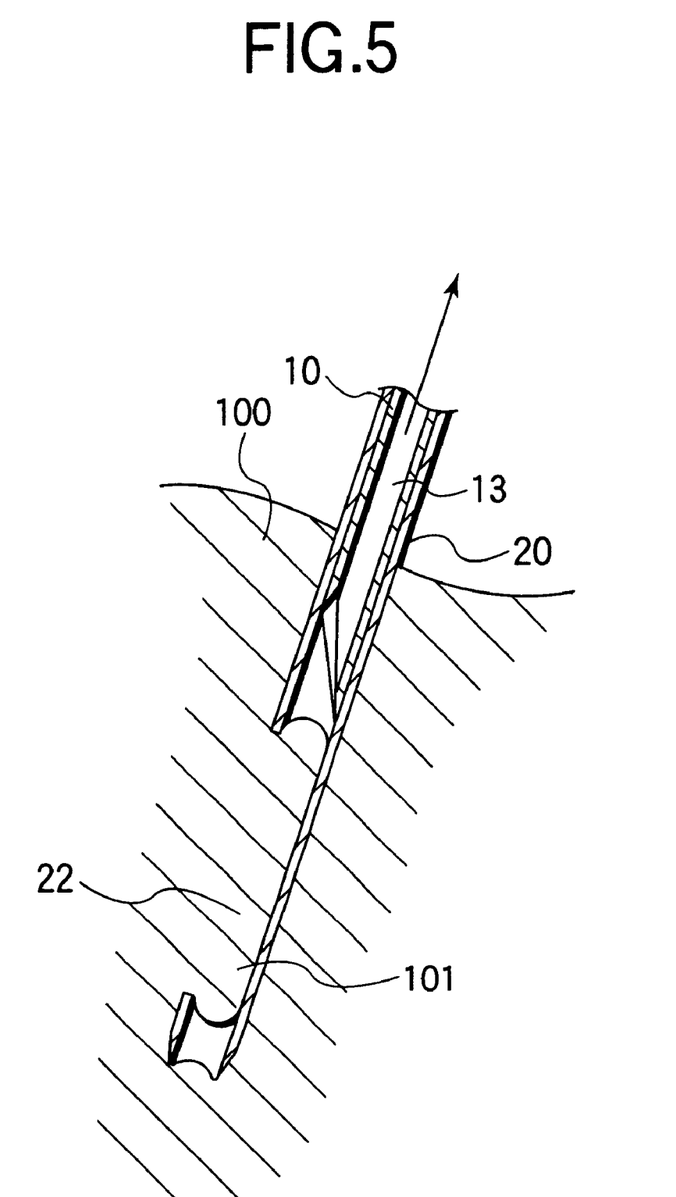
FIG. 5 is a longitudinal section showing the distal end portion of the endoscopic tissue collecting instrument as it is in the second phase of use.
Figure 6:
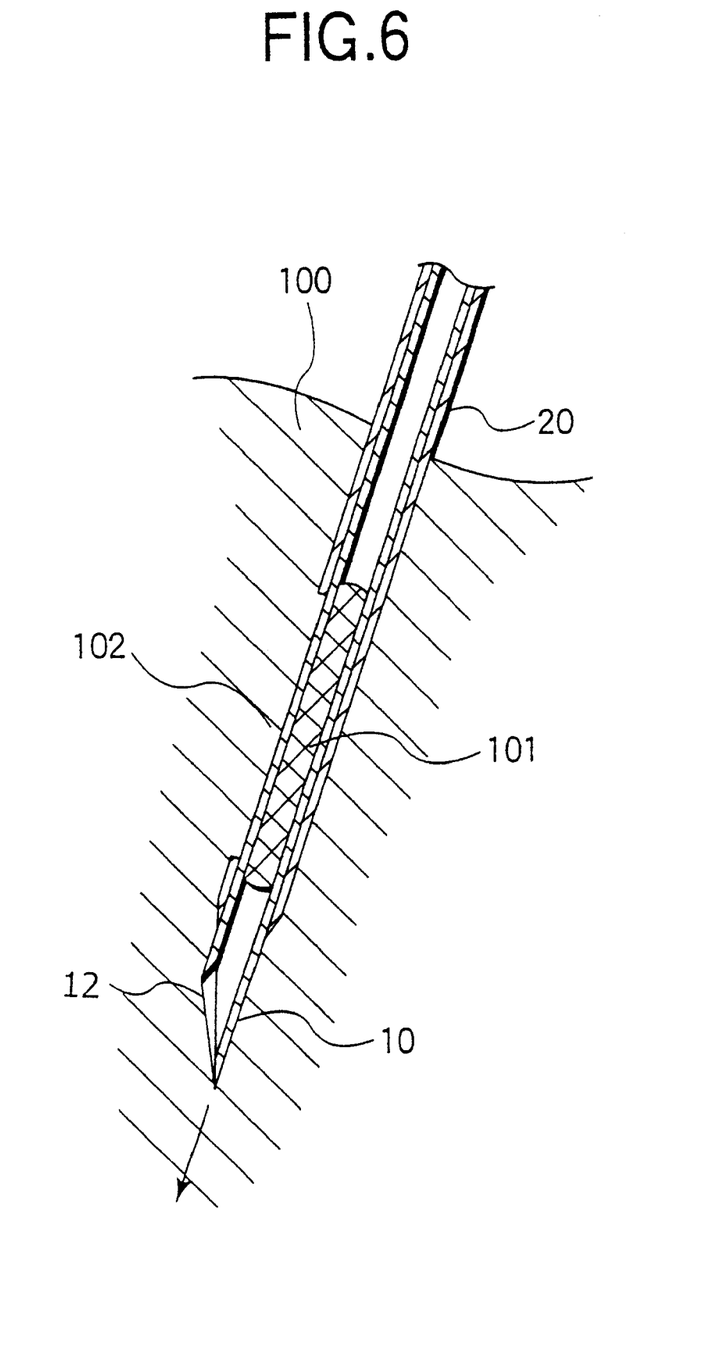
FIG. 6 is a longitudinal section showing the distal end portion of the endoscopic tissue collecting instrument as it is in the third phase of use.

FIGS. 4–6 show how a tissue specimen for biopsy is collected from the liver, the pancreas or other organ by means of the endoscopic tissue collecting instrument according to the embodiment described above. First, as shown in FIG. 4, the distal end of the inner needle 10 is allowed to protrude from the distal end of the outer sheath 20 so that the needle tip 11 is pierced into the tissue 100. Since the outer sheath 20 has the blade portion 21 at the distal end, the tissue collecting instrument can be smoothly pierced into the tissue.

When the tissue retaining recess 22 has reached a predetermined position in the tissue, the inner needle 10 is pulled toward the operator until the tissue retaining recess 22 becomes exposed and vacuum is drawn toward the operator via the aspiration channel 13 as shown in FIG. 5.

Then, the tissue specimen 101 which is a portion of the tissue 100 is aspirated into the outer sheath 20 via the tissue retaining recess 22. Hence, the thickness of the collected tissue specimen is exactly the same as the inside diameter of the outer sheath 20 and it is the largest size that can be secured with the given diameter of the outer sheath 20.

In the next step, with the tissue specimen 101 having been aspirated, the inner needle 10 is pushed forward as shown in FIG. 6, whereupon the tissue specimen 101 is cut off from the rest of the tissue 102 by the blade 12 of the inner needle 10 sliding along the inner surface of the outer sheath 20. The severed tissue specimen 101 is placed within the tissue retaining recess 22.

In this way, the tissue specimen 101 of a large size can be easily collected. Since the inner needle 10 slides within the outer sheath 20, it is smoothly pushed forward with a small sliding resistance. As is clear from FIG. 6, the tissue specimen 101 is collected within the inner needle 10 such that some part of the tissue specimen 101 is slightly compressed.

Figure 7:
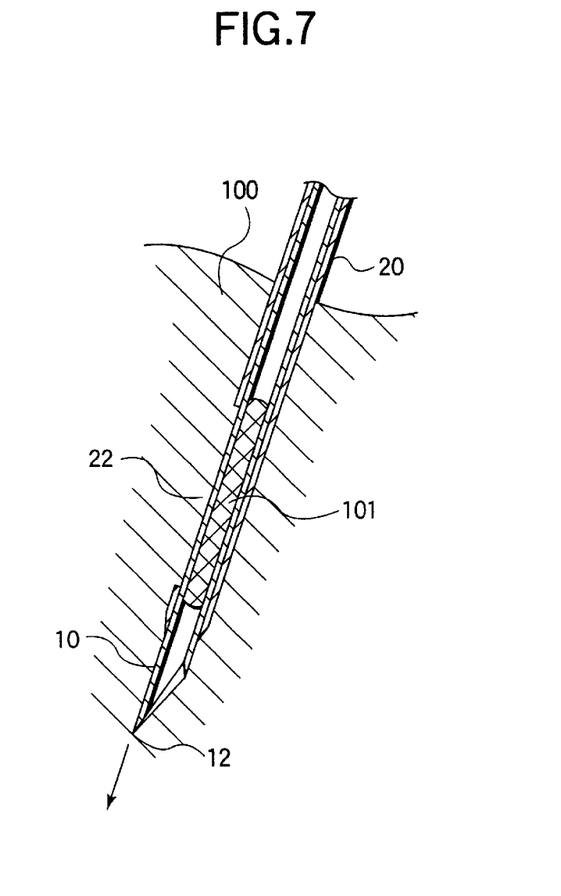
FIG. 7 is a longitudinal section showing the distal end portion of the endoscopic tissue collecting instrument as it is in the fourth phase of use.

Since the cutting blade 12 is formed at the distal end of the inner needle 10 on substantially all of its inner periphery, there is no limitation regarding a rotational position of the inner needle 10 relative to the outer sheath 20. Hence, the instrument may be used as shown in FIG. 7, that is, the positional relationship shown in FIG. 6 which concerns the rotation of the inner needle 10 relative to the outer sheath 20 may be reversed by 180 degrees as shown in FIG. 7.

Figure 8:
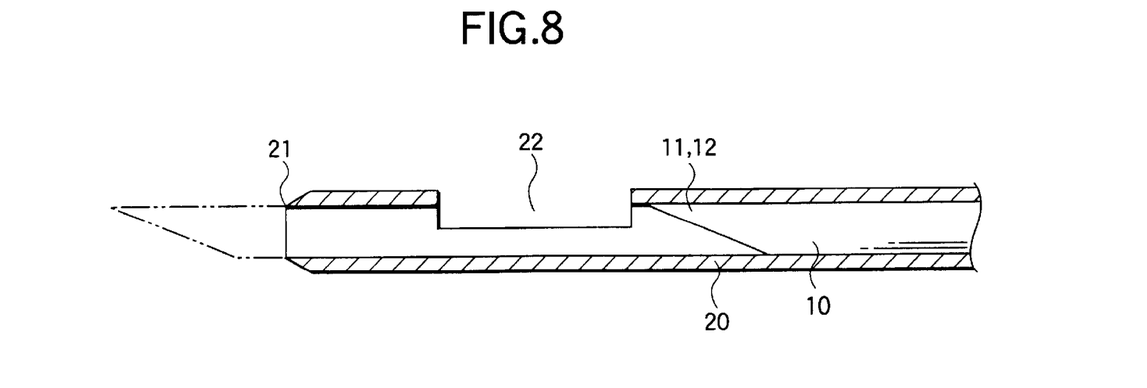
FIG. 8 is a longitudinal section showing the distal end of an endoscopic tissue collecting instrument according to the second embodiment of the invention.

The present invention is by no means limited to the embodiment described above and various modifications can be made. For example, the aspiration channel 13 may be formed in other areas than the bore of the inner needle 10, such as the boundary between the inner needle 10 and the outer sheath 20. If desired, the inner needle 10 may be formed as a solid rod that does not permit vacuum drawing as shown in FIG. 8.

Figure 9:
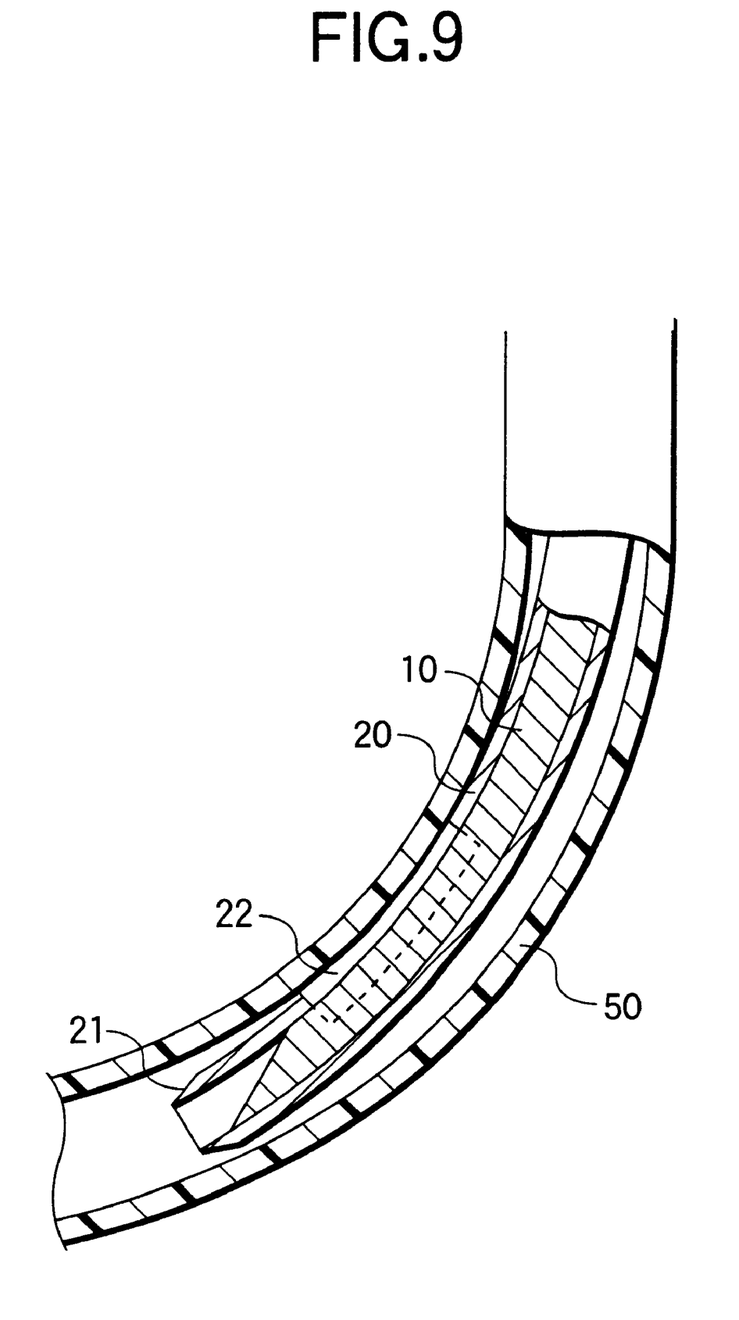
FIG. 9 is a longitudinal section showing how the endoscopic tissue collecting instrument is used without a guide tube.

The guide tube 30 is not an essential component. In certain cases such as where the treatment instrument insertion channel of an endoscope has a gentle curvature (see FIG. 9 in which the channel is indicated by 50), the tissue collecting instrument of the invention may be directly inserted into or removed from the treatment instrument insertion channel 50 with the distal end of the inner needle 10 being drawn into the outer sheath 20.

What is claimed is:

1. An endoscopic tissue collecting instrument comprising:
   an outer sheath including:
      an annular blade portion formed on an outer periphery of a distal end of the outer sheath and directed forwardly; and
      a tissue retaining recess formed in a lateral side of an area close to the blade portion; and
      an inner needle that is fitted into the outer sheath and capable of moving back and forth along a longitudinal axis, the inner needle including:
         a cutting blade, formed on an entire inner circumference at a distal end of the inner needle, for cutting off tissue entering the tissue retaining recess; and
         a needle tip formed at the distal end of the inner needle, and pointed forward, said needle tip being continuous with said cutting blade, wherein:
            the inner needle configured to be manipulated from an operator end to move back and forth between two positions, one being a position where the distal end of the inner needle is drawn into the outer sheath such that the inner needle does not close the tissue retaining recess and the other being a position where the inner needle protrudes from the distal end of the outer sheath.

2. The endoscopic tissue collecting instrument according to claim 1, wherein the distal end of the inner needle is in the form of a tube, and the cutting blade is formed on an inner periphery of the tube.

3. The endoscopic tissue collecting instrument according to claim 1, further comprising:
   an aspiration channel that communicates with the tissue retaining recess at a distal end thereof and which extends to a basal end of the outer sheath.

4. The endoscopic tissue collecting instrument according to claim 3, wherein the aspiration channel is formed in the inner needle, and a connection socket for establishing connection to an aspirating device is provided at a basal end of the inner needle.

5. The endoscopic tissue collecting instrument according to claim 1, wherein the tissue retaining recess is a cutout formed in the lateral side of said outer sheath.

6. The endoscopic tissue collecting instrument according to claim 1, further comprising:
   a guide tube through which the outer sheath is passed to be capable of moving back and forth along the longitudinal axis.

7. The endoscopic tissue collecting instrument according to claim 1, wherein the needle tip of the inner needle also serves as the cutting blade.

8. The endoscopic tissue collecting instrument according to claim 1, wherein said outer sheath is formed of a flexible member.

9. An endoscopic tissue collecting instrument comprising:
   a tubular outer sheath having a distal end opening and a lateral opening close to the distal end opening; and
   an inner needle having a slanted distal end defining a cutting blade formed on an entire inner circumference of the inner needle, and an opening circumscribed by the cutting blade, and an interior space extending from the opening, wherein the inner needle is slidably fitted into the outer sheath so that the slanted distal end of the inner needle can protrude from the distal end opening of the outer sheath and can be positioned behind the lateral opening.

10. An endoscopic tissue collecting instrument comprising:
    an outer sheath including:
       an annular blade portion formed on an outer periphery of a distal end of the outer sheath and directed forwardly; and
       a tissue retaining recess formed in a lateral side of an area close to the blade portion; and
       an inner needle that is fitted into the outer sheath and capable of moving back and forth along a longitudinal axis, the inner needle including:
          a cutting blade, formed at a distal end of the inner needle, for cutting off tissue entering the tissue retaining recess; and
          a needle tip formed at the distal end of the inner needle, and pointed forwardly, wherein:
             the endoscopic tissue collecting instrument is configured so that while the outer sheath remains stationary relative to surrounding tissue, the inner needle can be manipulated from an operator end to move back and forth between two positions, one being a position where the distal end of the inner needle is drawn into the outer sheath such that the inner needle does not close the tissue retaining recess so that a tissue sample from the surrounding tissue may be collected in the tissue retaining recess, and the other being a position where the inner needle protrudes from the distal end of the outer sheath.

11. An endoscopic tissue collecting instrument comprising:
    an outer sheath including:
       an annular blade portion formed on an outer periphery of a distal end of the outer sheath and directed forwardly; and
       a tissue retaining recess formed in a lateral side of an area close to the blade portion; and
       an inner needle that is fitted into the outer sheath and capable of moving back and forth along a longitudinal axis, the inner needle including:
          a cutting blade, formed at a distal end of the inner needle, for cutting off tissue entering the tissue retaining recess; and
          a needle tip formed at the distal end of the inner needle, and pointed forwardly, wherein:

the inner needle is configured to be manipulated from an operator end to move back and forth between two positions, one being a position where the distal end of the inner needle is drawn into the outer sheath such that the inner needle does not close the tissue retaining recess so that tissue may be collected in the tissue retaining recess by applying vacuum in the tissue retaining recess, and the other being a position where the inner needle is moved out of the distal end of the outer sheath to cut the tissue held by vacuum in the tissue retaining recess with the cutting blade at the distal end of the inner needle.

* * * * *

UNITED STATES PATENT AND TRADEMARK OFFICE
CERTIFICATE OF CORRECTION

PATENT NO.    : 6,656,132 B1
DATED         : December 2, 2003
INVENTOR(S)   : Teruo Ouchi It is certified that error appears in the above-identified patent and that said Letters Patent is hereby corrected as shown below:

<u>Title page,</u>
Item [73], Assignee, "Pentex Corporation" should be -- PENTAX Corporation --.

Signed and Sealed this

Twenty-third Day of March, 2004

JON W. DUDAS
*Acting Director of the United States Patent and Trademark Office*